(12) United States Patent
Phan et al.

(10) Patent No.: US 7,251,033 B1
(45) Date of Patent: Jul. 31, 2007

(54) IN-SITU RETICLE CONTAMINATION DETECTION SYSTEM AT EXPOSURE WAVELENGTH

(75) Inventors: Khoi Phan, San Jose, CA (US); Bhanwar Singh, Morgan Hill, CA (US); Bharath Rangarajan, Sunnyvale, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 455 days.

(21) Appl. No.: 10/858,757

(22) Filed: Jun. 2, 2004

(51) Int. Cl.
*G01N 21/00* (2006.01)

(52) U.S. Cl. ............................ 356/432; 356/433

(58) Field of Classification Search ............... None
See application file for complete search history.

(56) References Cited

U.S. PATENT DOCUMENTS 6,665,065 B1 * 12/2003 Phan et al. ............ 356/237.1
6,844,206 B1 * 1/2005 Phan et al. ................ 438/7

\* cited by examiner

*Primary Examiner*—Michael P. Stafira
(74) *Attorney, Agent, or Firm*—Amin, Turocy & Calvin, LLP

(57) ABSTRACT

A system and method are provided for detecting contaminants or defects on a reticle in-situ. The system and method provide a system that measures the optical transmission through clear areas on a reticle and determines whether the optical transmission of a reticle has been degraded by contaminants or other defects.

17 Claims, 12 Drawing Sheets

IN-SITU RETICLE CONTAMINATION DETECTION SYSTEM AT EXPOSURE WAVELENGTH

FIELD OF THE INVENTION

The present invention generally relates to semiconductor processing and, more particularly, to a system and method for detecting reticle contamination, in-situ, at the exposure wavelength.

BACKGROUND OF THE INVENTION

In the semiconductor industry, there is a continuing trend toward higher device densities. To achieve these high densities there have been, and continue to be, efforts toward scaling down device dimensions (e.g., at sub-micron levels) on semiconductor substrates. In order to accomplish such high device packing densities, smaller and smaller feature sizes are required. This includes the width and spacing of interconnecting lines, spacing and diameter of contact holes, and surface geometry such as corners and edges of various features. With an ever increasing number of integrated circuit features being formed on a semiconductor substrate, the amount of reticle or photomask contamination that may be tolerated without inducing defects in resulting semiconductor substrate has decreased. The importance of detecting contamination on a reticle or photomask, prior to semiconductor substrate exposure, has increased correspondingly.

Close spacing between adjacent small features requires high-resolution optical lithography. Optical lithography refers generally to the technology which enables etching patterns on a substrate through use of photographic development of images that have been attached onto the surface of the substrate using a mask. This technique is commonly used for integrated circuit fabrication in which a silicon structure is uniformly coated with a light-sensitive film, and an exposing source such as optical light, x-rays, or an electron beam illuminates selected areas of the surface through an intervening master template. The intervening master template is generally a reticle or photomask for a particular pattern. The lithographic coating is generally a light-sensitive coating suitable for receiving a projected image of the subject pattern. Once the image is projected, it is indelibly formed in the coating. The projected image may be either a negative or a positive image of the subject pattern. Exposure of the coating through a reticle or photomask causes the image area to become either more or less soluble, depending on the coating, in a particular solvent developer. The more soluble areas are removed in the developing process to leave the pattern image in the coating as less soluble polymer.

The process of manufacturing semiconductors employing reticles typically consists of more than one hundred steps. Generally, the process involves creating several patterned layers on and into a substrate that ultimately forms the complete integrated circuit. The patterned layers are created, in part, by the light that passes through the reticles. In order to achieve desired yield rates, reticles should be maintained relatively free of contamination throughout their use in the imaging process.

Unfortunately, during the manufacturing process, reticles may become contaminated. A contaminated reticle that goes undetected can result in the production of defective semiconductor substrates thereby reducing yield and efficiency of the fabrication process. With an ever-increasing number of integrated circuit features being formed on a semiconductor substrate, the importance of maintaining a reticle relatively free from contamination is increasing important. As the device feature dimensions reduce, lesser amounts or degrees of contamination may result in the production of defects in the semiconductor substrate. Therefore, detection of contamination is increasingly important to production line efficiency and yield.

Further exacerbating the situation, the trend towards higher device densities and smaller feature sizes requires substrate exposure at shorter wavelengths (193 nm, 157 nm). At such shorter wavelengths, defects such as haze or soft contamination grow on a reticle at a much faster rate than exposures at standard I-line (365 nm) or deep ultraviolet (248 nm) wavelengths. Soft contaminants and haze on a reticle block or reduce the amount of light that successfully passes through the clear portions of the reticle, thereby reducing the degree of exposure at the corresponding areas of the semiconductor substrate. The reduced exposure levels often result in corresponding defects in the exposed substrate.

Detection of contamination on a reticle is even more critical in step-and-repeat systems. Step-and-repeat systems repeatedly print a circuit pattern appearing on a reticle onto an area of a semiconductor substrate having photosensitive coating. This is accomplished by repeatedly projecting an image of the reticle onto successive portions of the semiconductor substrate. Such projection systems are used for device fabrication having reductions of greater than 1, typically 10:0 and 5:1, wherein the reticle contains a single copy or multiple copies of the device pattern to be employed. In step-and repeat systems, a defect on the reticle will be printed at every exposure location as the pattern is stepped and exposure is repeated across the semiconductor substrate. Thus, a semiconductor substrate defect resulting from a contaminated reticle will be created in all exposure locations on the semiconductor substrate. This significantly reduces yield and can result in an entire semiconductor substrate being unusable.

Conventional methods for contamination detection involve a man-in-the-loop inspection process whereby a person visually inspects the reticle or photomask at periodic intervals (e.g. once per day, once per week, etc.). Such methods are costly, time consuming, subject to the frailties of the human inspector, and cannot detect contamination or damage that may occur immediately following an inspection. For example, it is possible that a reticle may become contaminated or damaged while being moved from the inspection station to the lithographic imaging system. Furthermore, a reticle could be damaged while it is being loaded in the lithographic imaging system, may become contaminated while the patterning system is operating, or may become defective due to degradation of the reticle material. Such problems may remain undetected until the reticle is unloaded and reinspected, thereby allowing a significant amount of product to be processed with a resulting defect. Such problems drive production line yield and efficiency down and correspondingly increase product costs. More repeatable, consistent and timely methods of detecting defects are desirable to provide repeatable, consistent, cost effective and timely results.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

A system and method are provided for detecting contaminants and other similar defects on a reticle in-situ. The system and method provides for measuring optical transmission through clear areas of a reticle and determining whether the optical transmissive properties of the reticle have been degraded by contaminants, defects or other reasons. A detector is employed to measure and analyze light passing through the reticle, and if the transmitted light falls below a predetermined threshold, the system can label that reticle as not meeting proper constraints in connection with a particular lithographic process.

A reticle or photomask consists of an opaque layer upon a translucent substrate. The purpose of the opaque layer is to block light such that only areas that are translucent are imaged onto a photoresist deposited on a semiconductor substrate. As discussed above, it is possible that the reticle may become contaminated during its usage. In particular, at short exposure wavelengths (e.g. 193 nm, 157 nm, etc.) defects like haze or soft contaminants can grow at a much faster rate than standard I-line (365 nm) or deep ultraviolet (248 nm) exposure. The present invention utilizes the detector in conjunction with a processor to determine the amount of light transmission achieved through the reticle. If defects such as haze or soft contaminants have accumulated to a point where the light transmission through the reticle falls below a predetermined level, then the lithographic imaging process can be stopped and the reticle rejected.

A method in accordance with the invention provides for employing a detector to analyze a reticle prior to employment in a lithographic process. The detector provides an output that is a function of the amount of light received after passing through translucent areas of the reticle. A processor analyzes light detected by the detector, and makes a determination as to the sufficiency of light transmitted through the reticle—the determination can be based at least in part upon comparison to a predetermined threshold. The predetermined threshold corresponds to a degraded level of light transmission through the reticle. The processor determines whether the process should proceed or whether defects such as haze or other contaminants have degraded the reticle to a point where defects would be created in exposed semiconductor substrates.

A significant application of this method of contamination and defect detection is in optical lithographic imaging utilized in the manufacturing of integrated circuits such as semiconductor memory devices, microprocessors and other integrated circuits. Other applications include the manufacture of compact discs and other laser readable memory devices. The system and method of the present invention can be used to detect contamination and other defects on reticles or photmasks used not only for the above applications, but also for wiring patterns, word lines, bit lines, whole lines, and black patterns. Further, the application of this invention may be utilized in other applications requiring fine-line reticles or photomasks.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

The present invention will now be described with reference to the drawings. The following detailed description is of the best mode presently contemplated by the inventors for practicing the invention. It should be understood that the descriptions of these aspects are merely illustrative and that they should not be taken in a limiting sense.

As used in this application, the terms "component" and "system" are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. For example, an inference engine in accordance with the subject invention can comprise a Bayesian network, neural network, support vector machine (SVM), Hidden Markov Model, and any other suitable classifier-type system and/or methodology. It is to be appreciated that the subject invention can employ a utility analysis in connection with determining sufficiency of a reticle for an intended purpose, wherein the analysis can factor in the cost of making an incorrect determination. Accordingly, prior to rejecting a reticle, the subject invention can make additional queries, analysis in order to facilitate making a proper determination.

Figure 1:
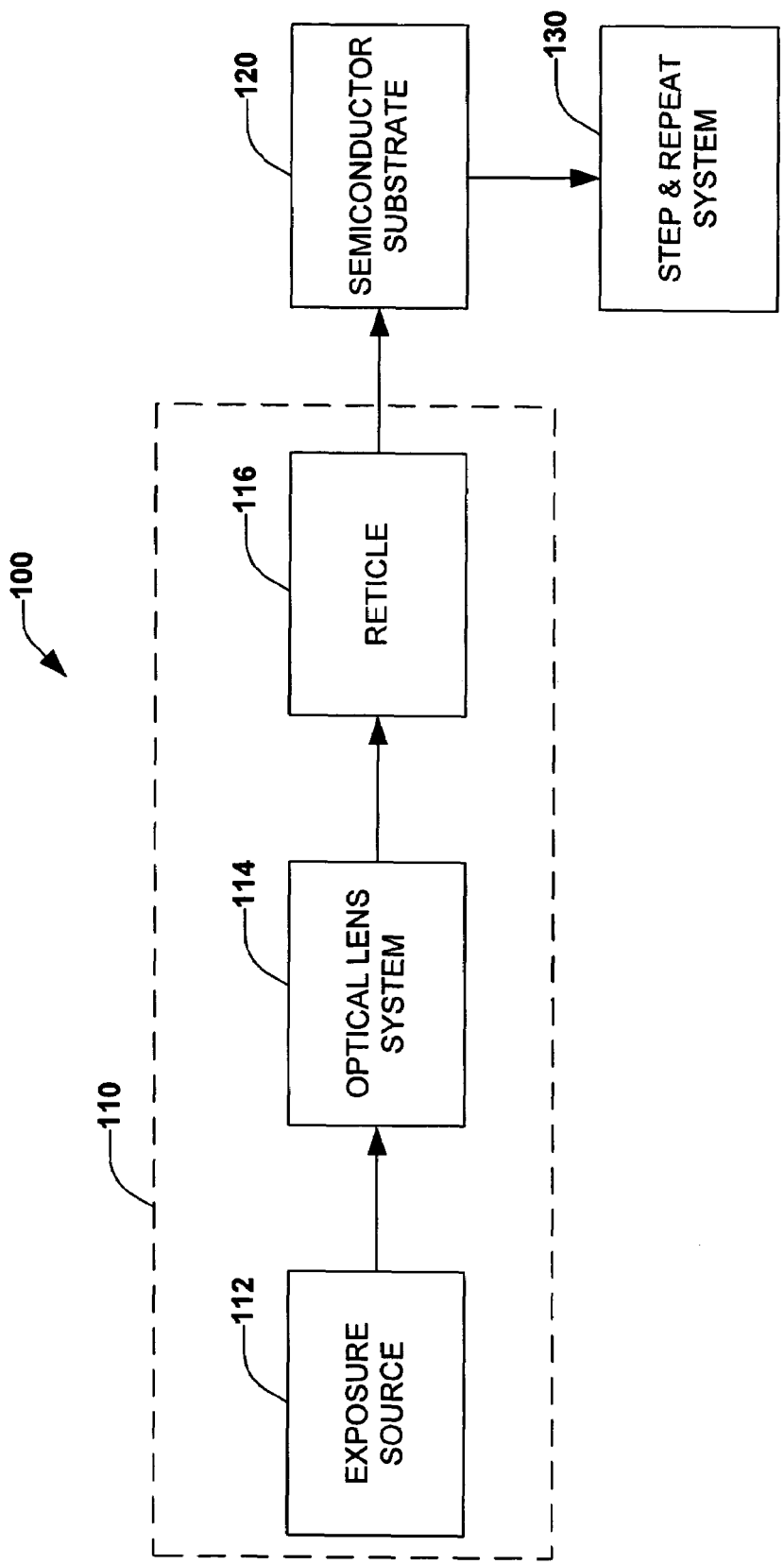
FIG. 1 is an illustration of a block diagram of a conventional lithographic imaging system.

FIG. 1 is an illustration of a block diagram of a conventional step and repeat lithographic imaging system. The imaging system 100 generally includes an optical system 110 for transferring a reticle pattern to a semiconductor substrate 120 and a stepper system 130 for stepping or indexing the semiconductor substrate 120 such that the reticle pattern may be repeatedly transferred to the semiconductor substrate 120. The optical system 110 generally includes an exposure source 112, an optical lens system 114, and a reticle (or photomask) 116 that contains the pattern that the system transfers to the semiconductor substrate 120. The step and repeat system 130 controls the position of the semiconductor substrate 120 relative to the optical system 110 and is typically aligned to any previous patterned layer.

Figure 2:
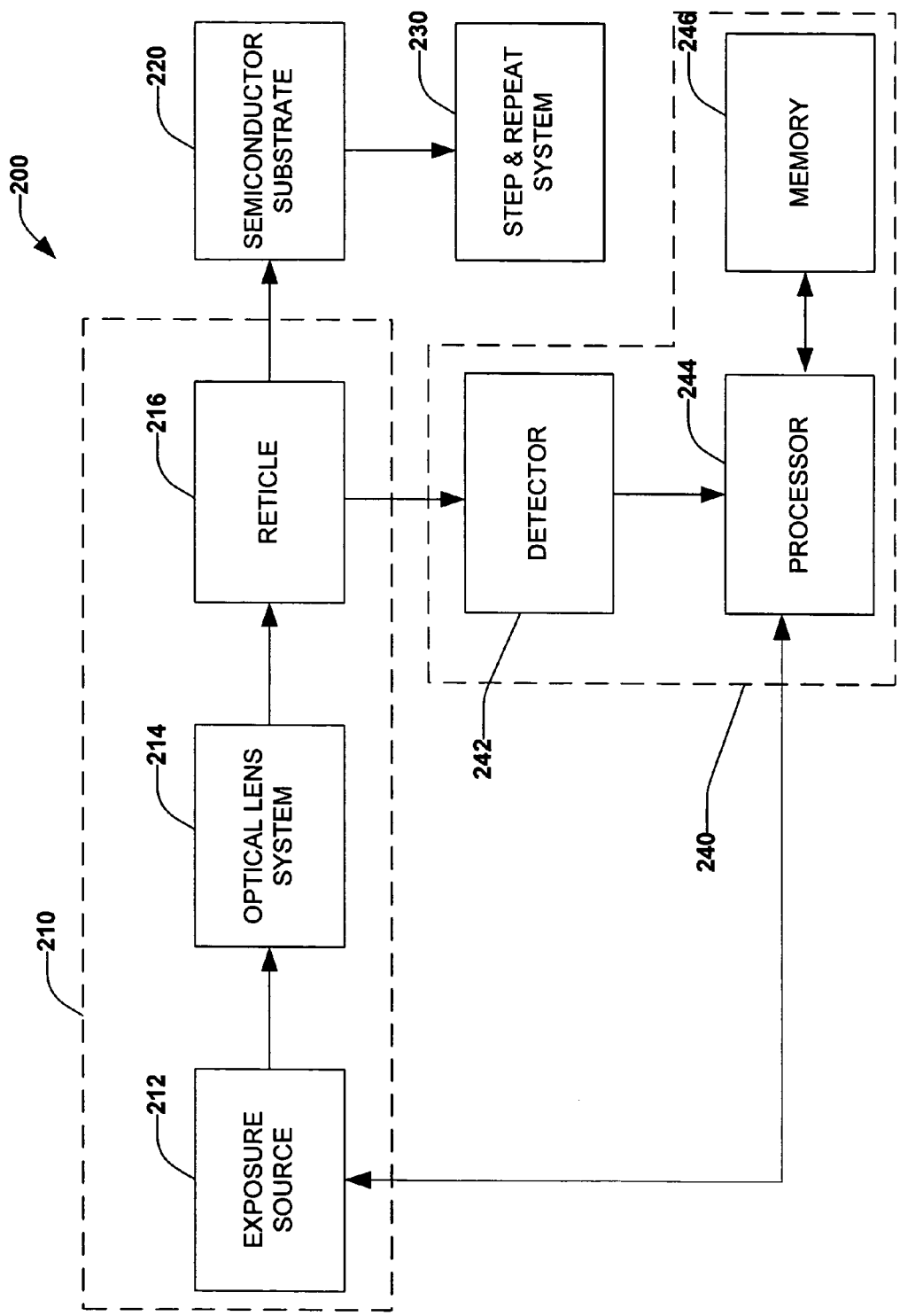
FIG. 2 is an illustration of a block diagram of a lithographic imaging system with a reticle contaminant detection system in accordance with an aspect of the invention.

FIG. 2 is an illustration of a block diagram of a lithographic imaging system 200 comprising a reticle contaminant detection system in accordance with an aspect of the present invention. The lithographic imaging system 200 generally includes an optical system 210 for transferring a reticle pattern to a semiconductor substrate, a semiconductor substrate 220, a step and repeat system 230 for stepping or indexing the semiconductor substrate, and a reticle contaminant detection system 240 for detecting contaminants on a reticle prior to exposure of the semiconductor substrate. Step and repeat system 230 generally includes a control system for controlling the position of the semiconductor substrate 220 relative to the optical system 210 and is typically aligned to any previous patterned layer. Optical system 210 generally includes an exposure source 212, an optical lens system 214, and a reticle (or photomask) 216 containing the pattern that the system transfers to the semiconductor substrate 220.

Conventional reticle inspection systems utilize exposure sources wherein the wavelength of the illumination employed is different than the wavelength actually employed during the lithographic imaging process. This can produce faulty inspection results as reticle contaminants such as haze may affect the transmissive properties of the reticle differently for different illumination wavelengths. Accordingly, it is possible to designate a "clean" reticle as contaminated or vice versa. In accordance with an aspect of the present invention, one and the same exposure source 212 is utilized both for inspection of the reticle and for lithographic imaging exposure of the semiconductor substrate. The results of the inspection are, therefore, always germane to the particular lithographic imaging system in question. Incorrect or inaccurate inspection assessments resulting from differences in the illumination wavelengths are eliminated. Exposure source 212 may be an $F_2$ laser beam (wavelength 157 nm), a high harmonic wave of YAG laser, and ArF excimer laser (wavelength 193 nm), KrF excimer laser (wavelength 248 nm), bright-lines emitted from a mercury lamp (such as g-line and i-line), or any other suitable source for exposure of the semiconductor substrate. In an alternate embodiment, a different exposure source is utilized for reticle inspection than for lithographic imaging, however, both sources employ illumination of the same, or approximately the same, wavelength.

Figure 3:
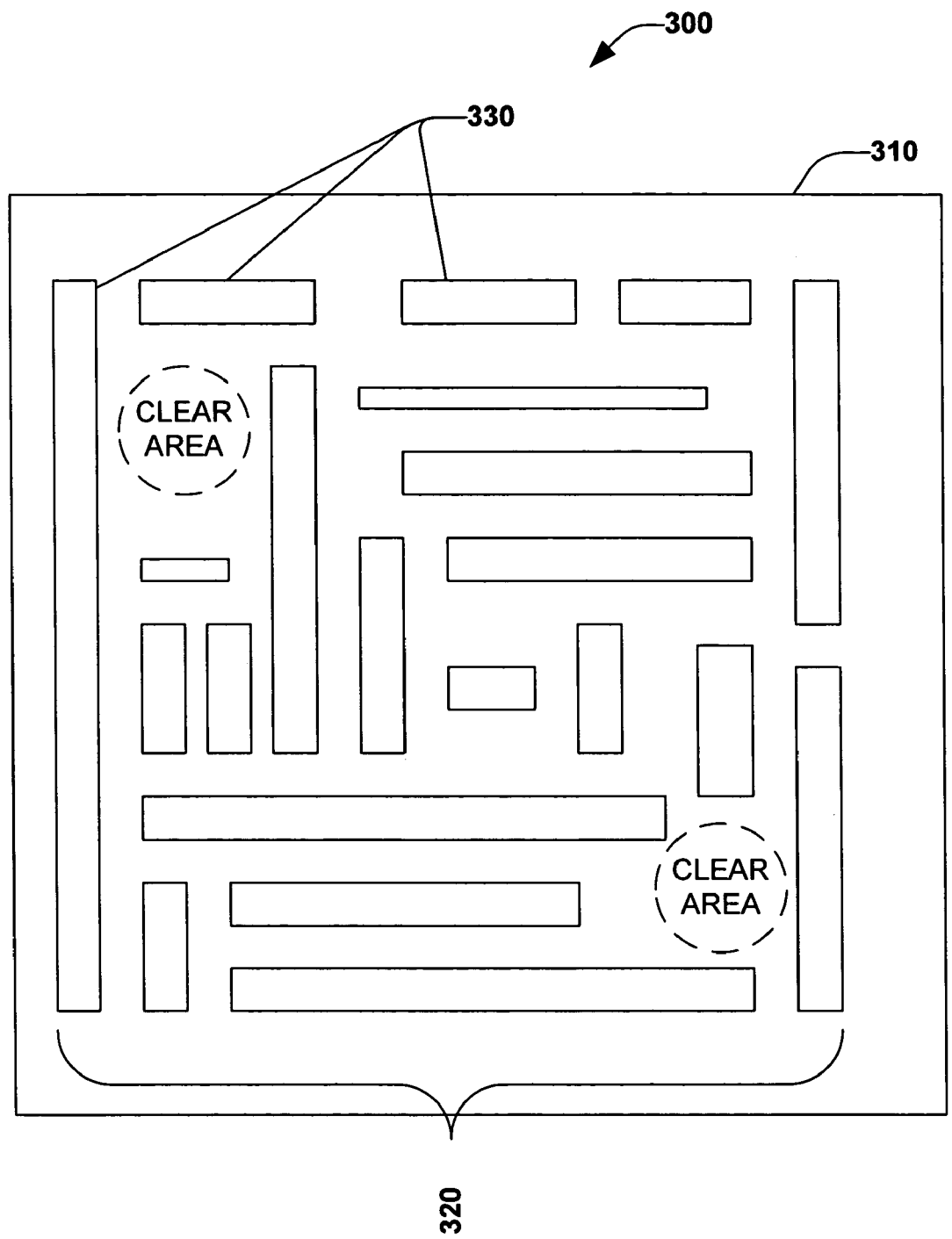
FIG. 3 is an illustration of a reticle.

In FIG. 2, reticle contaminant detection system 240 is operatively coupled to the optical system 210. Reticle contaminant detection system 240 comprises detector 242 operatively coupled to processor 244 that is operatively coupled to memory 246. It is understood that processor 244 may be a processor dedicated to determining the presence or absence of contaminants or, alternatively, may be a processor used to control one or more portions of the optical system 210 and/or step and repeat system 230. In one embodiment, detector 242 is temporarily positioned in the location that the semiconductor substrate is located during the lithographic imaging process. In another embodiment, detector 242 is permanently positioned near the location that the semiconductor substrate would normally occupy, but slightly farther from the exposure source. Detector 242 is coupled to optical system 210 such that light passing through reticle 216 will be incident on detector 242. Detector 242 is a photodetector, a photometer or any other type of device that provides an output that varies at least in part as a function of the light incident upon its surface. Detector 242 is coupled to processor 244 such that processor 244 receives the output of detector 242. Processor 244 compares the output of detector 242 with values stored within memory 246. Based on the output signal from detector 242 and values stored in memory 246, the processor determines whether the light incident on the detector is above or below a predetermined threshold level. The predetermined threshold level is established such that light levels above the threshold value will adequately expose the semiconductor substrate and light levels below the threshold value will not adequately expose the semiconductor substrate. If the light is passing through the reticle to the detector is greater than or equal to the predetermined threshold, the processor will allow the system to continue and allow the exposure of the semiconductor substrate. Alternatively, if the light passing through the reticle is below the predetermined threshold, the processor will prevent the system from continuing and prevent exposure of the semiconductor substrate. In one embodiment, detector 242 provides an output based on the average intensity of the illumination over the entire surface area of the detector. In another embodiment, detector 242 provides an output based on the illumination reaching a specified portion of detector 242 that corresponds to a specific clear area of the reticle. FIG. 3 illustrates the presence of multiple, relatively large clear areas 340 on reticle 300

Returning to FIG. 2, the lithographic imaging system 200 may, for example, be a 5× or 10× system in which the transferred pattern is reduced 5 or 10 times from the reticle to the substrate. However, it is understood that the exemplary imaging system is meant to be illustrative only and is not intended to limit the scope of the invention. It is understood that many different types of exposure sources, optical lens systems, and step-and-repeat (stepper) systems may be used with the present invention.

For example, the present invention my employ a variety of exposure sources. In one embodiment, exposure source 212 may be an $F_2$ laser beam (wavelength 157 nm), a high harmonic wave of YAG laser, and ArF excimer laser (wavelength 193 μm), KrF excimer laser (wavelength 248 μm), bright-lines emitted from a mercury lamp (such as g-line and i-line), or any other source suitable for exposure of the detector by illumination through the entire reticle. In another embodiment, exposure source 212 may employ a laser source wherein the source has the ability to scan selected portions of a reticle. For example, a laser source may selectively scan one or more of the large clear areas of a reticle (e.g., areas 340 of reticle 300 in FIG. 3) or any other portion of a reticle desired to be selectively examined. In yet another embodiment, the exposure source 212 may comprise more than a single source of illumination. For example, in accordance with the present invention, one embodiment comprises a broader wavelength illumination source that illuminates the detector through exposure of the entire reticle for a rapid inspection and a laser source that illuminates the detector by selectively scanning one or more of the large clear, or other selected, areas of the reticle. The preceding examples are illustrative of but a few alternative exposure sources and are not to be taken in a limiting sense.

Furthermore, although step and repeat system 230 and reticle contaminant detection system 240 are shown in FIG. 2 as separate systems for purposes of illustration, it is to be understood that the separate functions may be implemented differently. The individual functions of these systems may be combined in a different manner or integrated into a single system. For example, in one alternate embodiment, the functional elements of the reticle contaminant detection system are integrated with the step and repeat system. This single system provides all of functions described herein with regard to step and repeat system 230 and reticle contaminant detection system 240.

FIG. 3 is an illustration of a reticle typical of the type of reticle that is used in a step and repeat lithographic imaging system. In semiconductor integrated circuit fabrication, a reticle is used during the lithographic imaging process to expose a resist layer coated on a semiconductor substrate corresponding to the pattern formed on the reticle. Reticle 300 is illustrated as a brightfield reticle where patterned features to be transferred are opaque features on a clear background. However, it is to be understood that the principle and process of the invention may be applied to a darkfield reticle where the patterned features to be transferred are clear features on an, opaque background. Reticle substrate 310 can be any number of types of transparent material such as silica glass, fused quartz, or any other material transparent to the light commonly used in semiconductor lithographic operations. Overlying substrate 310 is an opaque metal layer 320 comprising a plurality of metal features 330. Metal layer 320 can be a composite material of chromium and gold, chromium and another metal, a homogeneous metal such as gold or other similar metals, or a combination of metals. During processing of the reticle, metal layer 320 is etched in order to leave a plurality of metal features 330. During lithographic imaging processes, the metal features 330 overlying translucent substrate 310 on the reticle 300 block light from passing through the reticle where the metal features are present. Large clear areas 340 exist where no opaque metal features block light from passing through the reticle. A semiconductor substrate will only be exposed by light that passes through the clear areas of the reticle.

Figure 4:
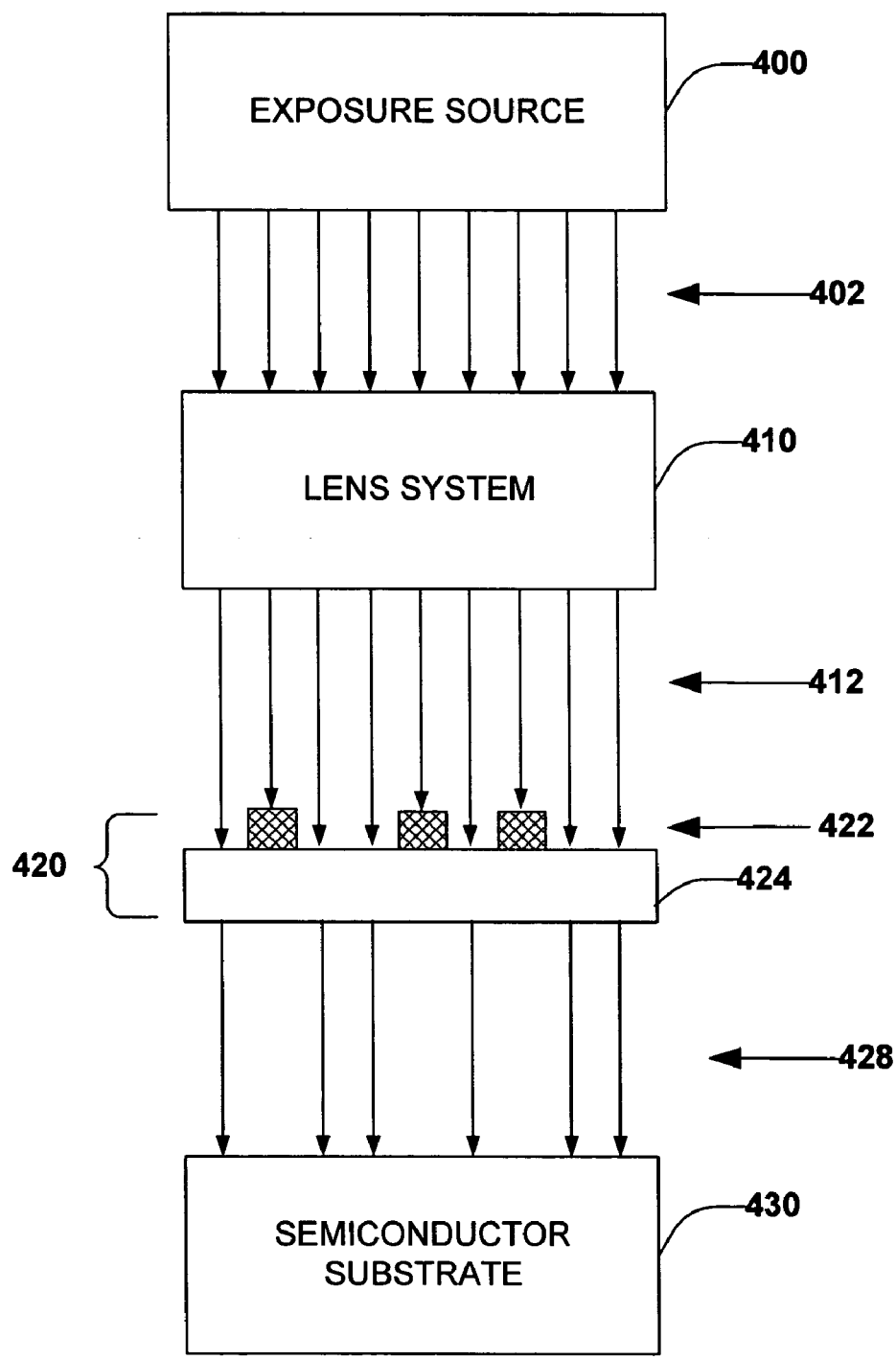
FIG. 4 is an illustration of light passing through a conventional lithographic imaging system.

This is illustrated in FIG. 4. Exposure source 400 emits light rays 402 (or other type of radiation suitable to expose the semiconductor substrate). Light shall be used in this description, but it is understood that any appropriate radiation may be used. Light rays 402 pass through lens system 410. Nearly 100% of the light 402 that is incident on the lens system 410 passes through the lens system and exits as light 412. Light 412 is incident on reticle 420. Some of the light 412 incident on reticle 420 is blocked by metal features in the opaque metal layer 422 of reticle 420. Another portion of light 412 is incident on only the translucent layer 424 and passes through and exits the reticle as light 428. Light 428 is incident on the semiconductor substrate 430.

Nearly all of the light intended to pass through the reticle must reach the semiconductor substrate in order for the pattern of the reticle to be ideally exposed onto the semiconductor substrate. Contaminants on the reticle reduce the ability of the reticle to pass through nearly all of the light incident on the reticle. For example, haze can grow on the surface of translucent portions of the reticle and reduce the amount of light that reaches the semiconductor substrate. Similarly, other contaminants on the translucent portion of the reticle may totally block light from passing through a certain portion of the reticle. Reticle contamination can result in an insufficient amount of light reaching the semiconductor substrate, thereby producing a defective semiconductor substrate. This situation is illustrated in FIG. 5.

Figure 5:
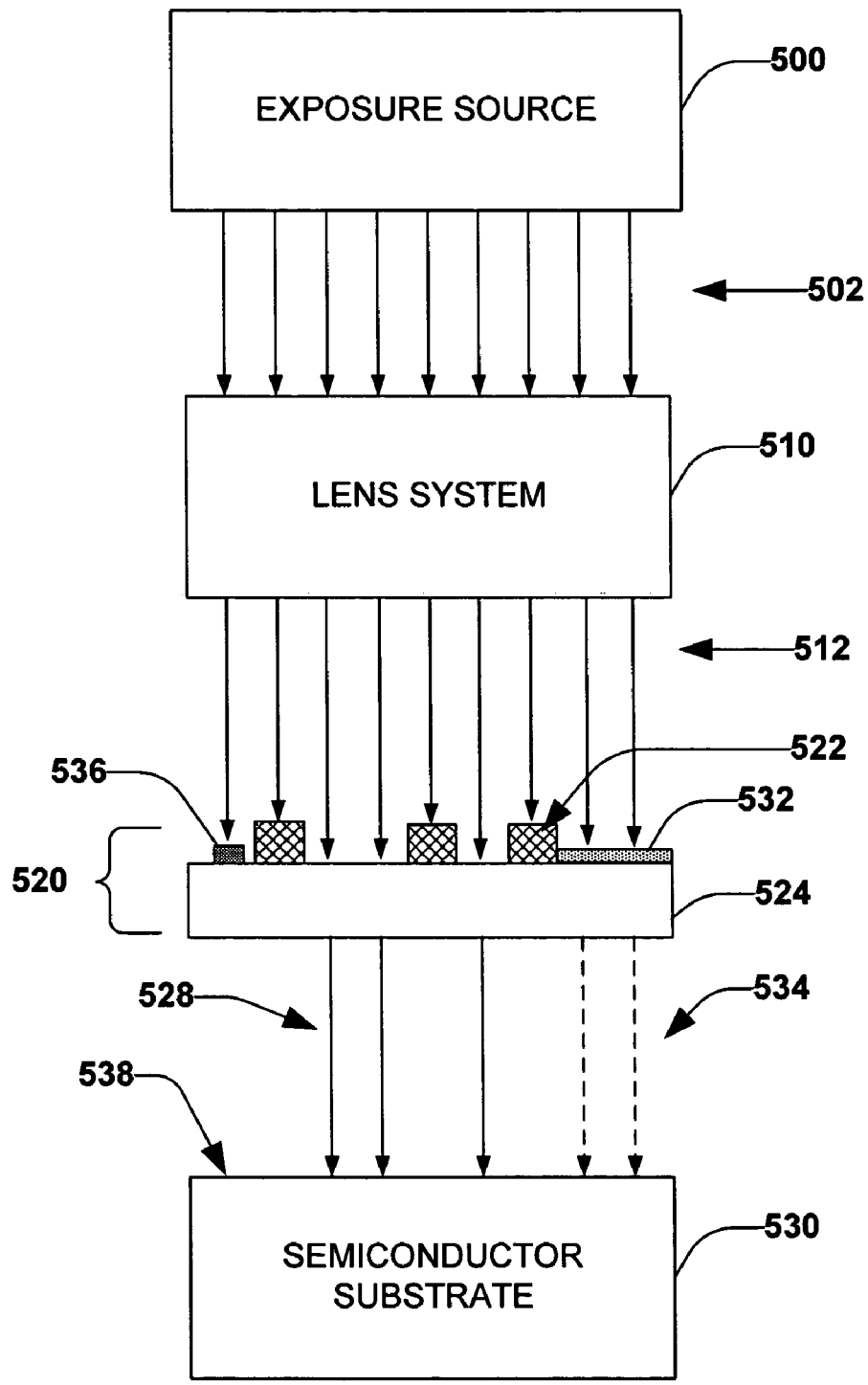
FIG. 5 is an illustration of light passing through a conventional lithographic imaging system wherein contaminants exist on a reticle.

In FIG. 5, exposure source 500 emits light rays 502 (or other type of radiation suitable to expose the semiconductor substrate). Light rays 502 pass through lens system 510. Nearly 100% of the light 502 that is incident on lens system 510 passes through and exits the lens system as light 512. Light 512 exiting the lens system 510 is incident on reticle 520. Some of the light 512 incident on reticle 520 is blocked by metal features in the opaque metal layer 522 of reticle 520. Another portion of light 512 will be incident on only the translucent layer 524 and will pass through the reticle as light 528. Light 528 is incident on the semiconductor substrate 530. Still another portion of light 512 incident on reticle 520 is incident on an area of the reticle where haze 532 has grown. This haze does not totally block the light incident upon it, but does filter out and/or scatter some of the light such that the intensity of the light 534 which passes through the haze covered portion of the reticle is reduced. Yet another portion of the light 512 incident on reticle 520 is incident in an area where contaminant 536 exists. Contaminant 536 partially or totally blocks the light that would otherwise pass through the reticle and be incident on semiconductor substrate 530 at 538.

Figure 6:
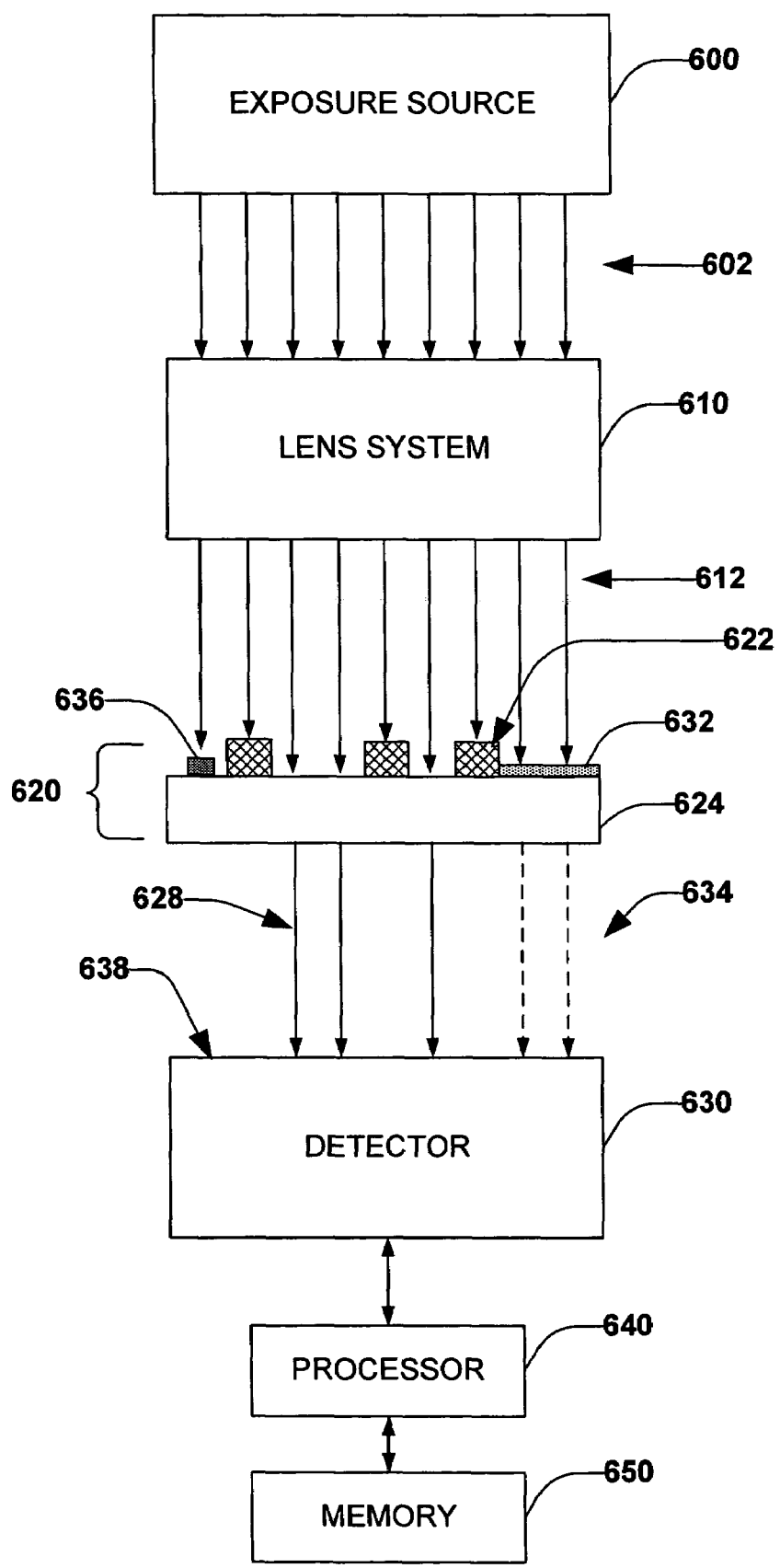
FIG. 6 is an illustration of light passing through a lithographic imaging system in accordance with an aspect of the present invention wherein contaminants exist on a reticle.

When haze or other contaminants on the reticle interfere with light reaching the semiconductor substrate, defects can be produced in the resulting product. FIG. 6 illustrates how a detector is used to measure the light passing through the reticle in accordance with an aspect of the invention. In FIG. 6, exposure source 600 emits light rays 602 or other type of radiation. Light rays 602 pass through lens system 610. Nearly 100% of the light 602 that is incident on the lens system 610 passes through and exits the lens system as light 612. Light 612 exiting the lens system 610 is incident on reticle 620. Some of the light 612 incident on reticle 620 is blocked by metal features in the opaque metal layer 622 of reticle 620. A portion of light 612 will be incident on only the translucent layer 624 and will pass through the reticle as light 628 incident on the detector 630. Still another portion of the light incident on reticle 620 is incident on an area of the reticle where haze 632 has grown. This haze does not totally block the light incident upon it, but does filter out and/or scatter some of the light such that the intensity of the light 634 which passes through the haze covered portion of the reticle is reduced. Yet another portion of the light incident on the on reticle 620 is incident in an area where contaminant 636 exists. Contaminant 636 totally blocks the light that would otherwise pass through the reticle and be incident on detector 630 at point 638.

Detector 630 is a photodetector, a photometer or any other type of device that provides an output that varies at least in part as a function of the radiation incident upon its surface. The output of detector 630 is coupled to processor 640. Processor 640 receives the output of detector 630. Processor 640 compares the output of detector 630 with values stored within memory 650. Based on the output signal from the detector 630 and values stored in memory 650, the processor determines whether the light incident on the detector is above or below a predetermined acceptable level. If the light is passing through the reticle to the detector is greater than or equal to the predetermined threshold, the processor will allow the system to continue and begin exposure of the semiconductor substrate. Alternatively, if the light passing through the reticle is below the predetermined threshold, the processor will prevent the system from continuing and prevent exposure of the semiconductor substrate.

It is to be appreciated that the invention is not limited to a static (above threshold, below threshold) type of analysis. For example, the subject invention can employ a probabilistic-based approach wherein the processor can include a classifier that has been partially or completely trained in connection with determining confidence levels in connection with a determination as to sufficiency of a reticle. Moreover, the classifier can be trained implicity (e.g., post-installment training via a user) in addition to being explicity trained.

Figure 7:
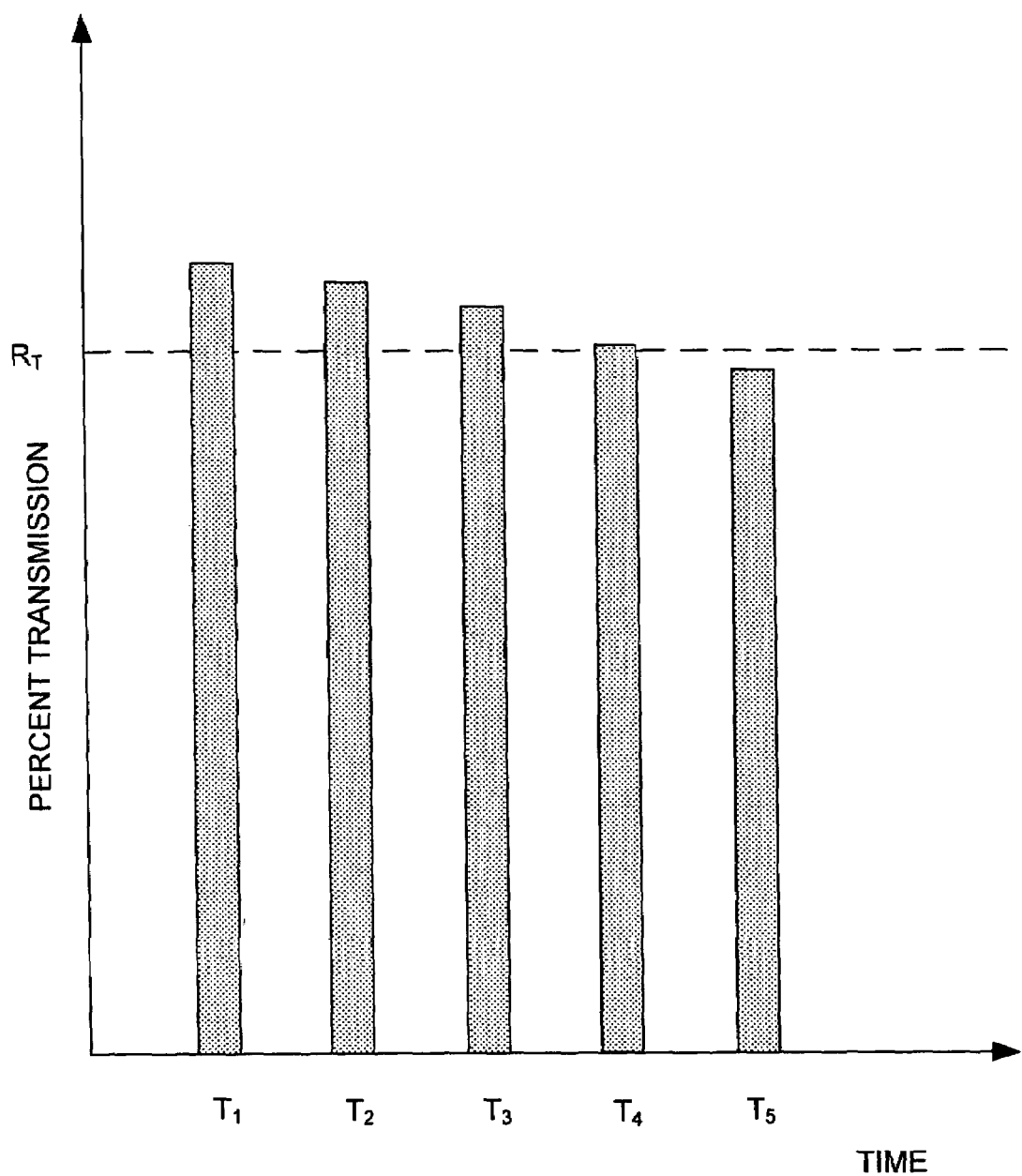
FIG. 7 is an illustration of a plot of the output of a detector in accordance with an aspect of the present invention.

FIG. 7 illustrates the output of a detector calibrated to correspond to a percentage of light transmission through a reticle. In accordance with an aspect of the invention, the system evaluates the amount of light that passes through the reticle and is incident upon the detector at periodic intervals. The system periodically exposes the detector to determine the amount of light received at the detector after passing through the reticle. The periodic intervals may be once per day, once per week, once per a predetermined number of uses, or any interval that is appropriate for the particular situation. $T_1$, $T_2$, $T_3$, $T_4$, and $T_5$ represent different times that the system exposed the detector to determine the amount of light received at the detector. RT represents a threshold level that has been predetermined such that a value greater than or equal to RT corresponds to a sufficient amount of light passing through the reticle and being received at the detector to adequately expose the semiconductor substrate. A value less than RT corresponds to an insufficient amount of light passing through the reticle and being received at the detector to adequately expose the semiconductor substrate. In FIG. 7, the output of the detector is expressed as a percentage of transmission. At $T_1$, the output of the detector, calibrated to correspond to percentage of transmission the through the reticle, is greater than RT and the process is allowed to continue. The same is true for $T_2$, $T_3$ and $T_4$ although each is output is successively closer to the threshold value. At $T_5$, the condition of the reticle has degraded to the point where the amount of light reaching the detector is below the threshold value and the process is stopped before the exposure of any semiconductor substrate.

Figure 8:
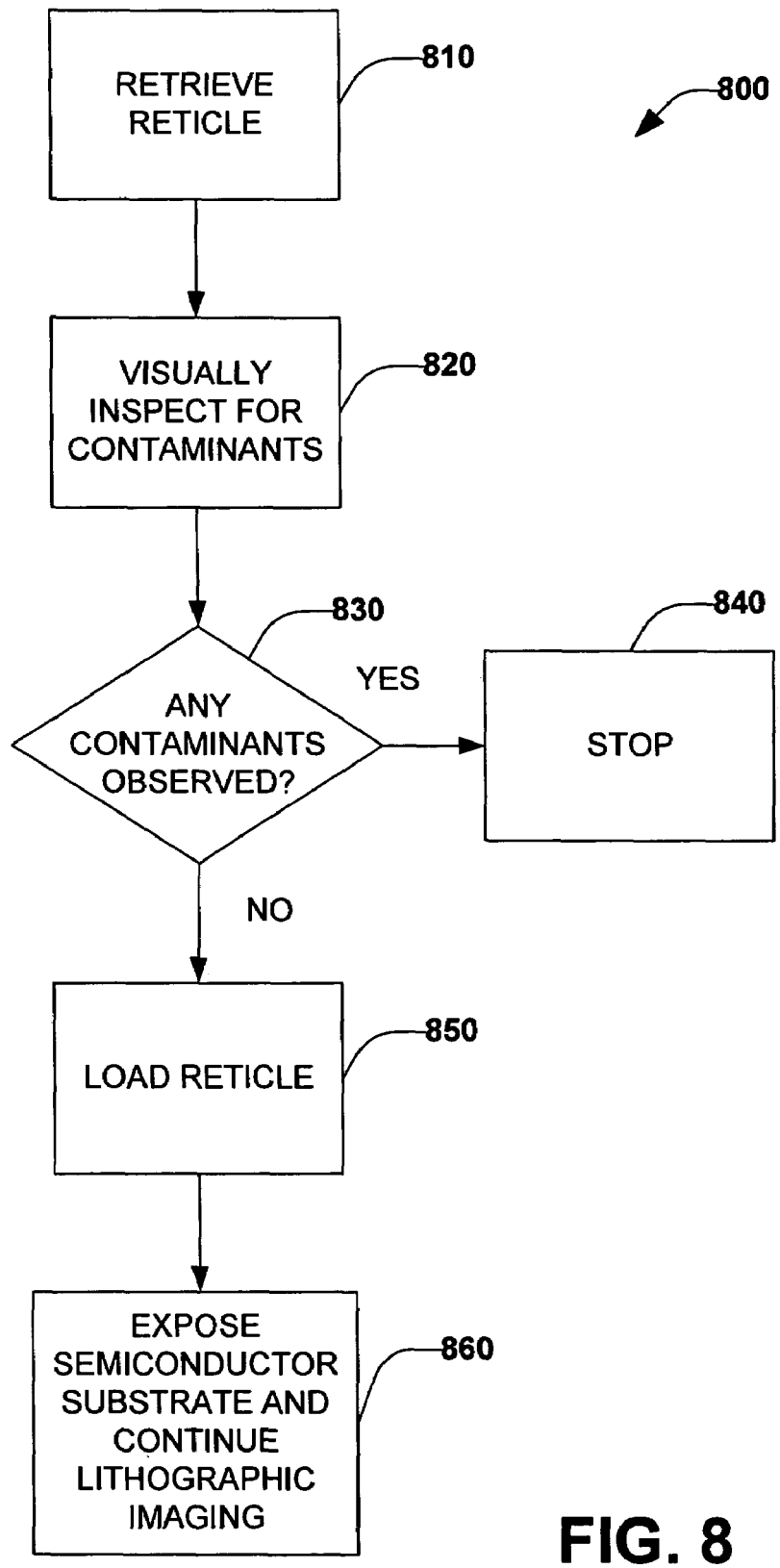
FIG. 8 is an illustration of a conventional methodology for visually inspecting a reticle for contaminants.

FIG. 8 illustrates one particular methodology 800 for inspecting a reticle for defects in accordance with a conventional method. The methodology begins at 810 where a reticle to be used in the lithographic imaging system is retrieved from the location in which it is stored. At 820 an individual visually inspects the reticle. The individual will look for obvious contaminants along with more subjective potential degradations. At 830 the individual makes a decision as to whether any contaminants that would interfere with the lithographic imaging process exist. If contamination is observed, then at 840 the methodology calls for stopping the lithographic imaging process. Consequently, the reticle is not loaded into the lithographic imaging system. Alternatively, if no contamination is observed at 830, then at 850 the reticle will be loaded into the stepper of the lithographic imaging system. At 860, the semiconductor substrate is exposed and the lithographic imaging processing continues until the next inspection interval.

Figure 9:
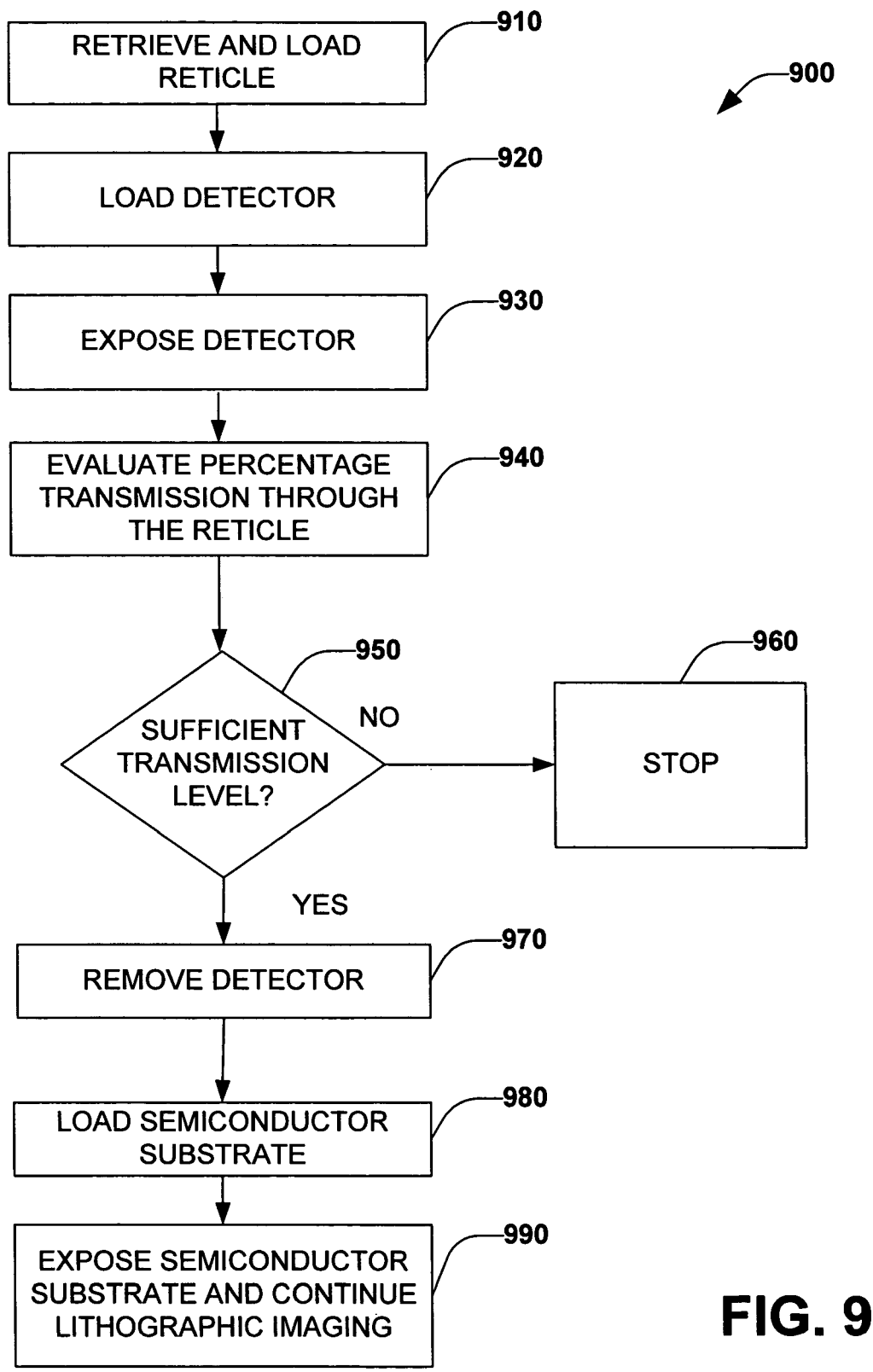
FIG. 9 is an illustration of a methodology of inspecting a reticle for contaminants in accordance with an aspect of the present invention.
Figure 10:
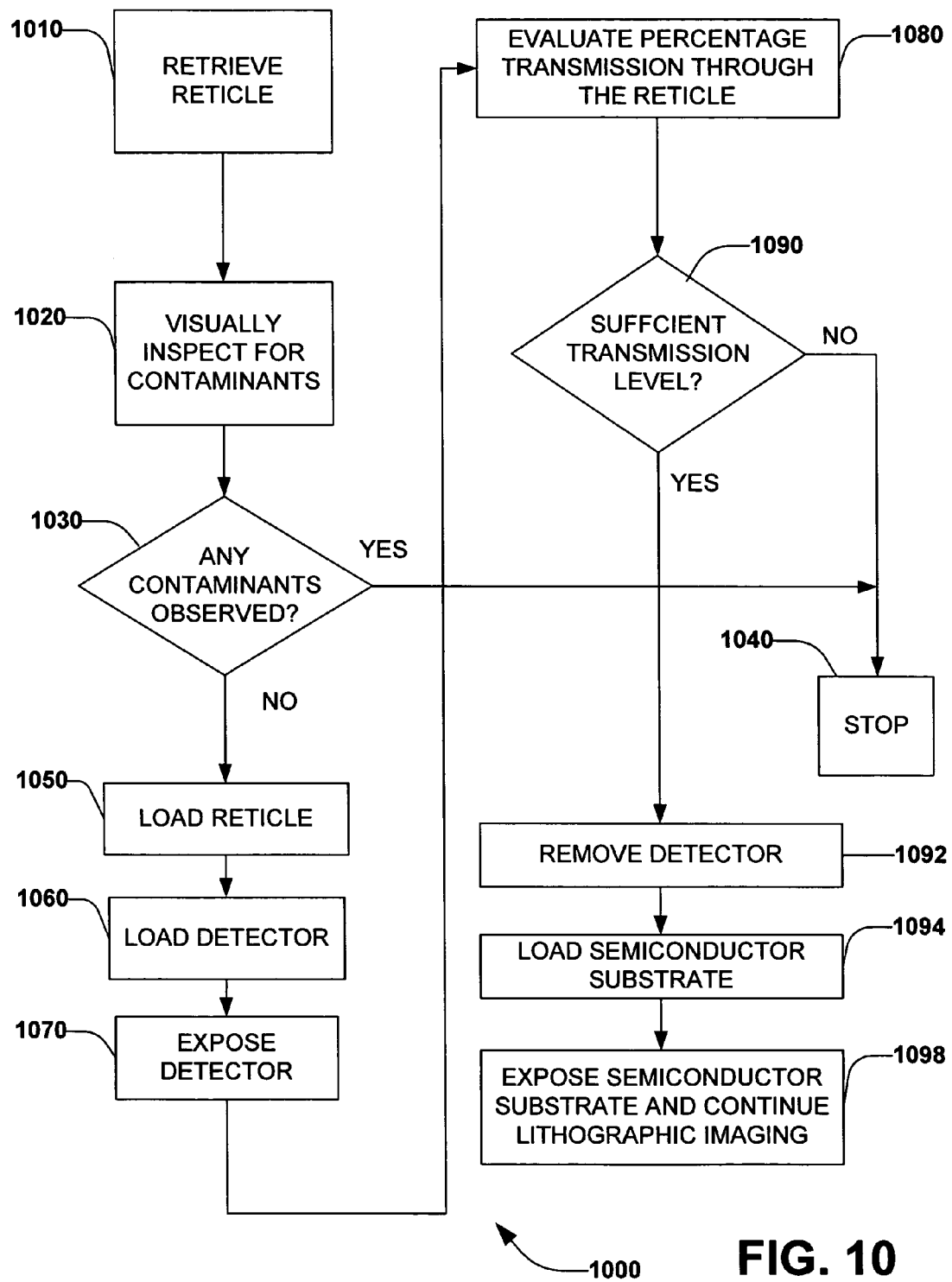
FIG. 10 is an illustration of a methodology of inspecting a reticle for contaminants in accordance with an aspect of the present invention.

In view of the foregoing structural and functional features described above, a methodology in accordance with various aspects of the present invention will be better appreciated with reference to FIG. 9 and FIG. 10. While, for purposes of simplicity of explanation, the methodology of FIG. 9 and FIG. 10 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 9 illustrates one particular methodology 900 for inspecting a reticle for contamination in accordance with an aspect of the invention. The methodology begins at 910 where the reticle is retrieved from its normal storage location and is loaded into the lithographic imaging system. At 920, a detector is loaded into system at a location where the semiconductor substrate would normally be located such that the light that would normally be incident on the semiconductor substrate will be incident on the detector. The detector can be a photodetector, a photometer or any other type of device that provides an output that varies at least in part as a function of the light incident upon its surface. At 930 the lithographic imaging system exposes the detector at the normal wavelength used for exposure of a semiconductor substrate. At 940, the detector output is used to determine the amount of light reaching the detector. The detector output may be based on the average illumination over the entire surface of the detector, or alternatively, may be based on the illumination reaching a specific area of the detector that corresponds to a specific clear area of the reticle. At 950, the processor compares the percentage transmission with a reference threshold value stored in memory and determines whether a sufficient amount of light is reaching the detector. If the exposure level is insufficient, the process is stopped at 960 before any semiconductor substrates are exposed. If the exposure level is sufficient, then at 970 the detector is removed and at 980 the semiconductor substrate is loaded into the imaging system. At 990, the semiconductor substrate is exposed and the imaging process continues.

FIG. 10 illustrates a methodology 1000 that combines a conventional visual inspection methodology with a methodology for evaluating a reticle for contaminants in accordance with an aspect of the invention. The methodology begins at 1010 where a reticle to be used in the processing is retrieved from the location in which it is stored. At 1020 an individual visually inspects the reticle for contaminants. The individual will look for obvious contaminants along with more subjective potential degradations. At 1030 the individual makes a decision as to whether any contaminants that would interfere with the lithographic imaging process exist. If contamination is observed, then at 1040 the methodology calls for stopping the lithographic imaging process. Consequently, the reticle is not loaded into the lithographic imaging system. Alternatively, if no contaminants are observed at 1030, then at 1050 the reticle will be loaded into the lithographic imaging system. At 1060, a detector is loaded into the system at a location where the semiconductor substrate would normally be located such that the light that would normally be incident on the semiconductor substrate is incident on the detector. The detector can be a photodetector, a photometer or any other type of device that provides an output that varies at least in part as a function of the light incident upon its surface. At 1070, the lithographic imaging system exposes the detector at the normal wavelength used for exposure of a semiconductor substrate. At 1080 the detector output is used to determine the amount of light reaching the detector. The detector output may be based on the average illumination over the entire surface of the detector or alternatively, may be based on the illumination reaching a specific area of the detector that corresponds to a specific clear area of the reticle. At 1090, the processor compares the percentage transmission with a reference threshold value stored in memory and determines whether a sufficient amount of light is reaching the detector. If the exposure level is insufficient, the process is stopped at 1040 before any semiconductor substrates are exposed. If the exposure level is sufficient, then at 1092 the detector is removed and at 1094 the semiconductor substrate is loaded into the imaging system. At 1098, the semiconductor substrate is exposed and the lithographic imaging process continues.

Figure 11:
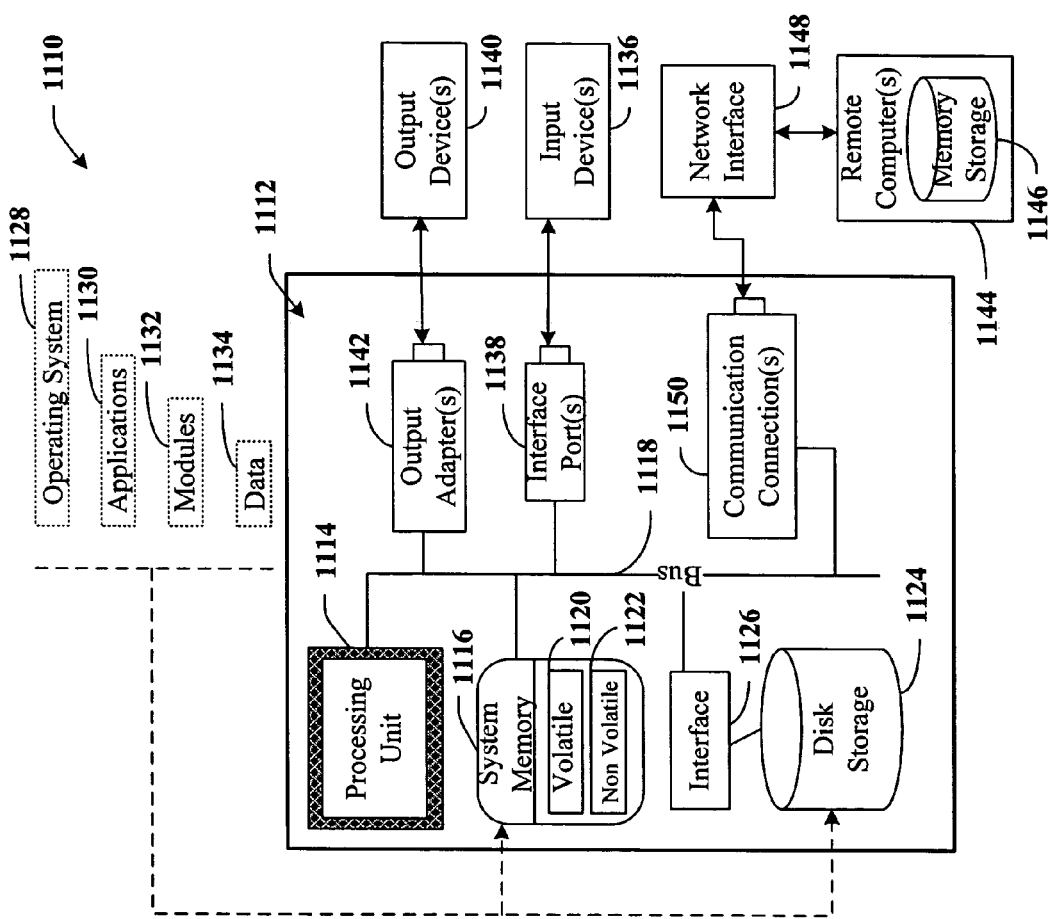
FIGS. 11 and 12 illustrate exemplary computing systems and/or environments in connection with facilitating employment of the subject invention.
Figure 12:
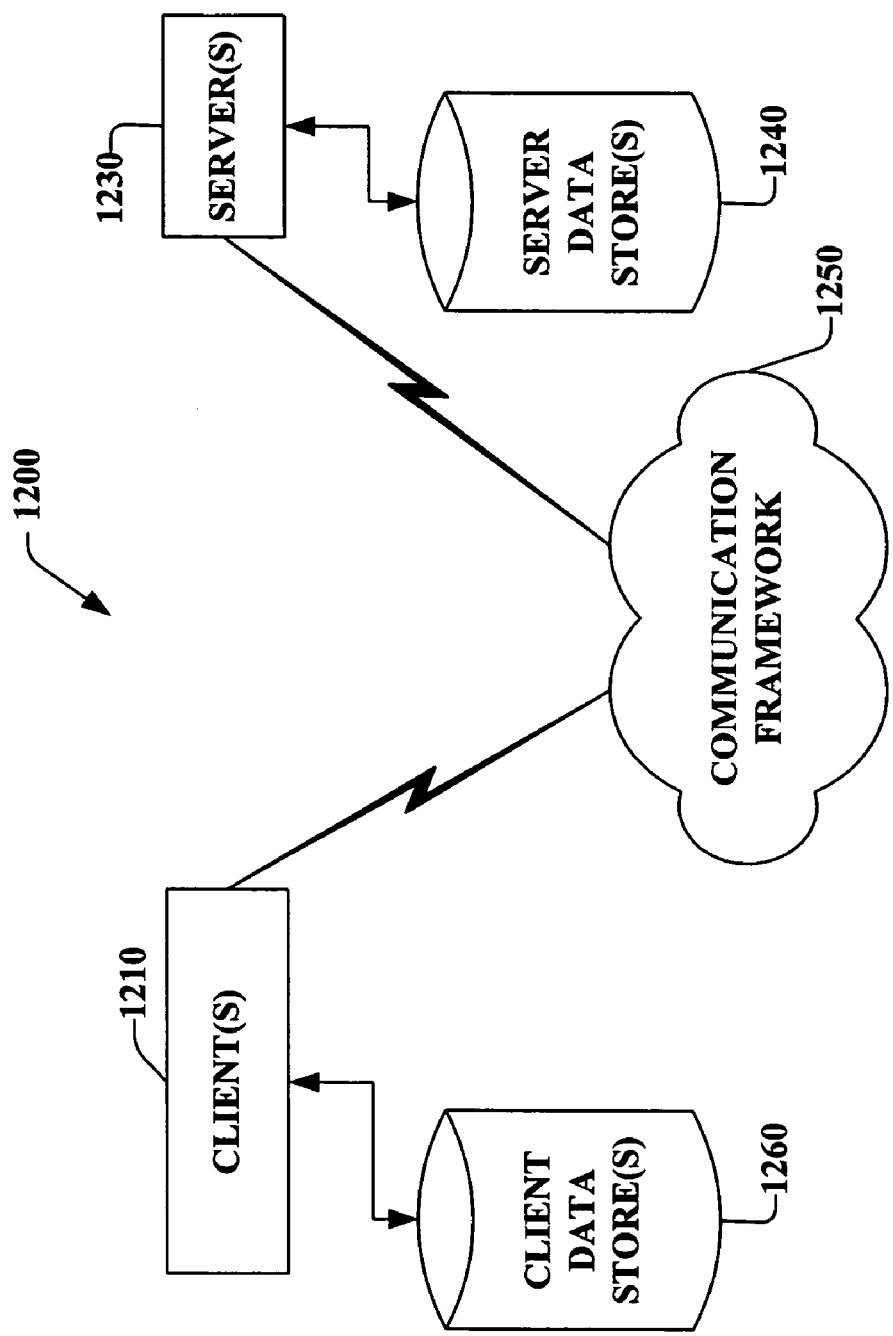

In order to provide a context for the various aspects of the invention, FIGS. 11 and 12 as well as the following discussion are intended to provide a brief, general description of a suitable computing environment in which the various aspects of the present invention may be implemented. While the invention has been described above in the general context of computer-executable instructions of a computer program that runs on a computer and/or computers, those skilled in the art will recognize that the invention also may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, handheld computing devices, microprocessor-based or programmable consumer electronics, and the like. The illustrated aspects of the invention may also be practiced in distributed computing environments where task are performed by remote processing devices that are linked through a communications network. However, some, if not all aspects of the invention can be practices on stand alone computers. In a distributed computing environment, program modules may be locate in both local and remote memory storage devices.

With reference to FIG. 1, an exemplary environment 1110 for implementing various aspects of the invention includes a computer 1112. The computer 1112 includes a processing unit 1114, a system memory 1116, and a system bus 1118. The system bus 1118 couples system components including, but not limited to, the system memory 1116 to the processing unit 1114. The processing unit 1114 can be any of various available processors. Dual microprocessors and other multiprocessor architectures also can be employed as the processing unit 1114.

The system bus 1118 can be any of several types of bus structure(s) including the memory bus or memory controller, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The system memory 1116 includes volatile memory 1120 and nonvolatile memory 1122. The basic input/output system (BIOS), containing the basic routines to transfer information between elements within the computer 1112, such as during start-up, is stored in nonvolatile memory 1122. By way of illustration, and not limitation, nonvolatile memory 1122 can include read only memory (ROM), programmable ROM (PROM), electrically programmable ROM (EPROM), electrically erasable ROM (EEPROM), or flash memory. Volatile memory 1120 includes random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

Computer 1112 also includes removable/non-removable, volatile/non-volatile computer storage media. FIG. 11 illustrates, for example a disk storage 1124. Disk storage 1124 includes, but is not limited to, devices like a magnetic disk drive, floppy disk drive, tape drive, Jaz drive, Zip drive, LS-100 drive, flash memory card, or memory stick. In addition, disk storage 1124 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1124 to the system bus 1118, a removable or non-removable interface is typically used such as interface 1126.

It is to be appreciated that FIG. 11 describes software that acts as an intermediary between users and the basic computer resources described in suitable operating environment 1110. Such software includes an operating system 1128. Operating system 1128, which can be stored on disk storage 1124, acts to control and allocate resources of the computer system 1112. System applications 1130 take advantage of the management of resources by operating system 1128 through program modules 1132 and program data 1134 stored either in system memory 1116 or on disk storage 1124. It is to be appreciated that the present invention can be implemented with various operating systems or combinations of operating systems.

A user enters commands or information into the computer 1112 through input device(s) 1136. Input devices 1136 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1114 through the system bus 1118 via interface port(s) 1138. Interface port(s) 1138 include, for example, a serial port, a parallel port, a game port, and a universal serial bus (USB). Output device(s) 1140 use some of the same type of ports as input device(s) 1136. Thus, for example, a USB port may be used to provide input to computer 1112, and to output information from computer 1112 to an output device 1140. Output adapter 1142 is provided to illustrate that there are some output devices 1140 like monitors, speakers, and printers, among other output devices 1140, that require special adapters. The output adapters 1142 include, by way of illustration and not limitation, video and sound cards that provide a means of connection between the output device 1140 and the system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. The remote computer(s) 1144 can be a personal computer, a server, a router, a network PC, a workstation, a microprocessor based appliance, a peer device or other common network node and the like, and typically includes many or all of the elements described relative to computer 1112. For purposes of brevity, only a memory storage device 1146 is illustrated with remote computer(s) 1144. Remote computer(s) 1144 is logically connected to computer 1112 through a network interface 1148 and then physically connected via communication connection 1150. Network interface 1148 encompasses communication networks such as local-area networks (LAN) and wide-area networks (WAN). LAN technologies include Fiber Distributed Data Interface (FDDI), Copper Distributed Data Interface (CDDI), Ethernet/IEEE 1102.3, Token Ring/IEEE 1102.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1150 refers to the hardware/software employed to connect the network interface 1148 to the bus 1118. While communication connection 1150 is shown for illustrative clarity inside computer 1112, it can also be external to computer 1112. The hardware/software necessary for connection to the network interface 1148 includes, for exemplary purposes only, internal and external technologies such as, modems including regular telephone grade modems, cable modems and DSL modems, ISDN adapters, and Ethernet cards.

FIG. 11 is a schematic block diagram of a sample-computing environment 1200 with which the present invention can interact. The system 1200 includes one or more client(s) 1210. The client(s) 1210 can be hardware and/or software (e.g., threads, processes, computing devices). The system 1200 also includes one or more server(s) 1230. The server(s) 1230 can also be hardware and/or software (e.g., threads, processes, computing devices). The servers 1230 can house threads to perform transformations by employing the present invention, for example. One possible communication between a client 1210 and a server 1230 may be in the form of a data packet adapted to be transmitted between two or more computer processes. The system 1200 includes a communication framework 1250 that can be employed to facilitate communications between the client(s) 1210 and the server(s) 1230. The client(s) 1210 are operably connected to one or more client data store(s) 1260 that can be employed to store information local to the client(s) 1210. Similarly, the server(s) 1230 are operably connected to one or more server data store(s) 1240 that can be employed to store information local to the servers 1230.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An in-situ reticle contaminant detection system comprising:
   a component that receives light transmitted through a reticle; and
   an analyzing component that probabilistically analyzes the transmitted light, based at least in part upon properties of the light being compared against predetermined thresholds, the processor outputting a determination as to sufficiency of the reticle for a particular lithographic process based upon the analyzed light.

2. The system of claim 1 wherein the light receiving component comprises a photodetector.

3. The system of claim 1, the analyzing component comprises a processor.

4. The system of claim 1, the analyzing component is software executed on a processor.

5. The system of claim 1 further comprising a memory that stores a plurality of predetermined thresholds corresponding respectively to a plurality of lithographic processes.

6. The system of claim 5, the memory further stores exposure data corresponding to the processes.

7. The system of claim 1, further comprising an inference engine that performs a probabilistic and/or statistical analysis in connection with determining the sufficiency of the reticle, the analysis factoring utility of the reticle as well as cost associated with making an incorrect determination regarding the sufficiency of the reticle.

8. The system of claim 1, further comprising an exposure source that provides illumination with a wavelength of about 193 nm.

9. The system of claim 8 wherein the exposure source is an ArF excimer laser.

10. The system of claim 8 wherein the exposure source also provides illumination with a wavelength of about 157 nm.

11. The system of claim 8 wherein the exposure source is an $F_2$ laser beam.

12. The system of claim 1 further comprising a lens system.

13. A step and repeat system comprising the system of claim 1.

14. The system of claim 1 measures an average intensity of illumination from an exposure source incident on a surface of a detector.

15. The system of claim 14 wherein the detector measures the intensity of illumination from the exposure source incident on a specified portion of the detectors surface.

16. An in-situ reticle contaminant detection system comprising:
- means for receiving light transmitted through a reticle;
- means for storing predetermined values relating to a lithographic process; and
- means for probabilistically analyzing the transmitted light, based at least in part upon properties of the light compared against predetermined thresholds, the processor outputting a determination as to sufficiency of the reticle for the lithographic process based upon the analyzed light.

17. A method for analyzing sufficiency of a reticle in a lithographic imaging system, comprising:
- receiving light transmitted through the reticle;
- probabilistically analyzing the received light, the analysis based at least in part upon a comparison to threshold values;
- determining a sufficiency value of the reticle based upon the analysis; and
- storing the sufficiency value in a computer readable memory.

* * * * *